United States Patent [19]

von Bittera et al.

[11] 4,189,467

[45] Feb. 19, 1980

[54] POLYURETHANES HAVING ECTOPARASITICIDAL ACTIVITY

[75] Inventors: Miklos von Bittera, Leverkusen; Hans U. Sieveking, Cologne; Wilhelm Stendel, Wuppertal; Herbert Voege, Leverkusen, all of Fed. Rep. of Germany

[73] Assignee: Bayer Aktiengesellschaft, Leverkusen, Fed. Rep. of Germany

[21] Appl. No.: 891,094

[22] Filed: Mar. 28, 1978

[30] Foreign Application Priority Data

Apr. 7, 1977 [DE] Fed. Rep. of Germany ....... 2715595
Apr. 7, 1977 [DE] Fed. Rep. of Germany ....... 2715596
Dec. 29, 1977 [DE] Fed. Rep. of Germany ....... 2758571

[51] Int. Cl.$^2$ .................. A01K 27/00; A01K 29/00; A01M 1/20; A01N 17/08
[52] U.S. Cl. .................................... 424/14; 424/16; 424/28; 424/78; 119/106; 119/156
[58] Field of Search ................ 424/14, 16, 27, 28, 424/78–83; 119/106, 156–160

[56] References Cited

U.S. PATENT DOCUMENTS

| 2,205,711 | 6/1940 | Banks | 119/106 |
|---|---|---|---|
| 2,621,163 | 12/1952 | Coash | 424/81 |
| 2,734,483 | 2/1956 | Peo | 119/160 |
| 2,791,202 | 5/1957 | Doyle | 119/106 |
| 2,966,440 | 12/1960 | Gerolt | 424/78 |
| 3,005,747 | 10/1961 | Jacobi | 424/78 |
| 3,227,563 | 1/1966 | Fahlstrom | 106/15 |
| 3,295,246 | 1/1967 | Landsman et al. | 424/27 X |
| 3,308,082 | 3/1967 | Pauli et al. | 424/78 |
| 3,400,093 | 9/1968 | Feinberg | 260/29.6 |
| 3,852,416 | 12/1974 | Grubb et al. | 424/14 |
| 3,904,746 | 9/1975 | Aries | 424/28 |
| 3,996,348 | 12/1976 | Greenberg | 424/78 |

FOREIGN PATENT DOCUMENTS

| 2124776 | 9/1972 | France | 424/28 |
|---|---|---|---|
| 2237580 | 3/1975 | France | 424/28 |
| 2267045 | 11/1975 | France | 424/28 |
| 2269859 | 12/1975 | France | 424/28 |
| 2307466 | 11/1976 | France | 424/28 |
| 1444038 | 7/1976 | United Kingdom | 424/219 |

*Primary Examiner*—Shep K. Rose
*Attorney, Agent, or Firm*—Gene Harsh; Joseph C. Gil

[57] ABSTRACT

The instant invention relates to plastic compositions having ectoparasiticidal activity, and, in particular, insecticidal and acaricidal, which contain particular ectoparasiticides and polyurethanes, and to animal collars comprising such plastics compositions.

11 Claims, 1 Drawing Figure

POLYURETHANES HAVING ECTOPARASITICIDAL ACTIVITY

BACKGROUND OF THE INVENTION

Animal collars having ectoparasiticidal activity have been known for some years. By using them, it is possible to protect animals and, in particular, small animals (especially dogs and cats) against infestation by *Mallophaga* and *Siphonaptera* and, in some cases, against *Ixodidae*.

In general, the ectoparasiticidally active animal collars available consist of thermoplastic polyvinyl chloride, into which an insecticidal active compound, usually O,O-dimethyldichlorovinyl phosphate (DDVP), has been incorporated by co-extrusion with the polyvinyl chloride. However, collars based on DDVP lead to the occasional occurrence of skin irritation on the animal. Additionally, the relatively short life of the collar as a result of the relatively high vapor pressure of DDVP ($1.2 \times 10^{-1}$ mm Hg) is also a disadvantage.

Animal collars based on plasticized thermoplastic polymers (preferably plasticized polyvinyl chloride) and which contain the less highly volatile carbamates as insecticidal active compounds are known and are described in U.S. Pat. No. 3,852,416. Whereas highly volatile active compounds such as DDVP rapidly pass directly into the gas phase from the ectoparasiticidally active plastic collars, insecticides of lower volatility, such as the above-noted carbamates, diffuse slowly out of the collar and form a white, dusty layer on its surface. Some of the active compound passes into the vapor phase by sublimation and is active there and some is distributed, in the form of a dust, over the animal to be treated.

The deposition of the active compound on the surface of the collar (known as "efflorescence" or "exudation") is associated with a number of disadvantages:

(1) When the collar is stored for a prolonged period before use, a relatively large amount of the active compound diffuses to the surface and becomes concentrated there. When the collar is used, there is then a very high dose of the insecticide on the surface, which while ensuring good immediate action, may also reach the point of being toxic to the animal.

(2) While the active compound present on the surface is rubbed off rapidly, the active substance in the deeper layers of the collar diffuses to the surface very slowly. Thus, the release of the insecticide is not linear over as long as possible a period as is desired and/or necessary.

(3) Finally, the dusty, whitish active compound present on the surface of the animal collar imparts an extremely unattractive, dusty or moldy appearance to the collar.

Plasticized polymers (such as, e.g. vinyl polymers, polyesters, polyurethanes and epoxide resins) are known and are described as carriers for various insecticides in French Pat. No. 1,568,194. The materials are employed in the form of a tape or powder, for example, for combating insects. Carbamates are not mentioned among the suitable insecticides disclosed therein.

Pulverulent, water-soluble vinyl polymers which contain various active compounds, including carbamates to be used as insecticides, are also known (see, e.g. U.S. Pat. No. 3,576,760). These polymer powders make it possible to apply an active compound in the dry form, for example to the earth's surface, where it is then released through the action of water.

U.S. Pat. Nos. 3,822,238 and 3,975,350 relate to hydrophilic, water-absorbing polyurethanes and polyurethane hydrogels and their use as carriers for various active substances. Insecticides are mentioned quite generally as such active compounds (for example those described in U.S. Pat. No. 3,576,760). However, the materials described therein would be unsuitable for the purposes of the instant invention because of their swellability in water.

BRIEF DESCRIPTION OF THE DRAWING

The drawing represents a graph comparison of the active ingredient release times among collars produced according to the instant invention and prior art collars.

DESCRIPTION OF THE INVENTION

Figure 1:
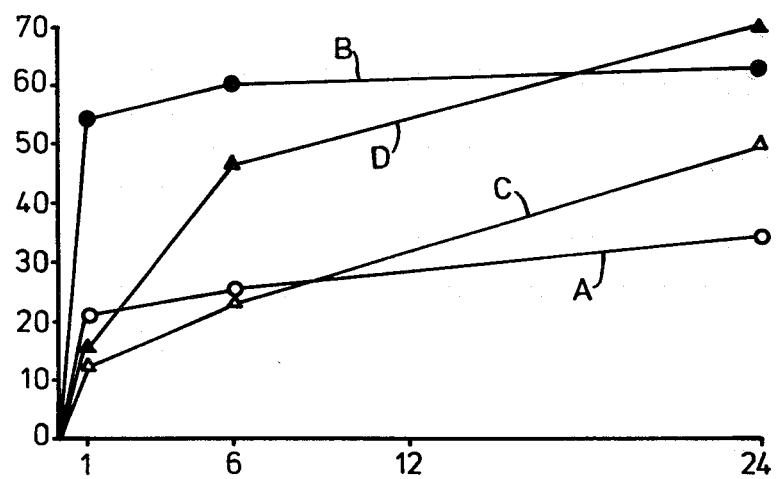

The present invention now provides a plastic composition having ectoparasiticidal activity, which comprises from 75 to 98%, and preferably from 85 to 95%, by weight of a hydrophobic polyurethane which is not swellable in water and from 2 to 25%, preferably from 5 to 15%, by weight of an ectoparasiticidal carbamate having a vapor pressure of from $10^{-4}$ to $10^{-6}$ mm Hg at 20° C.

The present invention also relates to an animal collar having ectoparasiticidal activity, which comprises such a plastic composition.

In addition to an industrially uncomplicated preparation process, the collars, according to the instant invention, have, above all, the advantage that the active compound is continuously released from them over a period of some months in an essentially linear manner. In fact, surprisingly, the active compound diffuses out of the polyurethane onto the surface in such a controlled manner that from there it is uniformly released into the surroundings by sublimation or by contact with the animal's fur. No noticeable efflorescence forms on the surface, so that a pleasant appearance of the collar is preserved, even on prolonged storage, and no toxicity problems occur. Compared with conventional PVC collars, the period of activity is also substantially extended.

The invention also provides a method of protecting or freeing an animal from ectoparasites which comprises fitting the animal with a collar of the instant invention.

By "hydrophobic" and "not swellable" as used herein and as used in the claims is meant polyurethane resins which, when immersed in water at 20° C. as a foil having a thickness of 2 mm, take up less than 2% by weight, and preferably less than 0.5% by weight, of water by swelling in the course of 24 hours.

Ectoparasiticides which can be used according to the invention are carbamates with a vapor pressure of from $10^{-4}$ to $10^{-6}$ mm Hg at 20° C. Compounds of this type are known and are described, for example, in U.S. Pat. No. 3,852,416, the disclosure of which is herein incorporated by reference. Their preparation is described in U.S. Pat. Nos. 2,903,478 and 3,203,853, both disclosures of which are herein incorporated by reference. Preferably, 2-isopropoxyphenyl-N-methylcarbamate ("Propoxur"), which has a vapor pressure of $6.5 \times 10^{-6}$ mm Hg, is employed as the ectoparasiticidal component.

Examples of other carbamates which are suitable include 3-tolyl-N-methylcarbamate, 3,4-xylyl-N-methyl-carbamate, m-(1-methylbutyl)-phenyl-N-methylcarbamate, (2-ethylthio-methyl-phenyl)-N-methylcarbamate, 4-dimethylamino-m-tolyl-N-methylcarbamate, 2,3-dihydro-2,2-dimethylbenzfuran-7-yl-N-methylcarbamate, 2-dimethylcarbamoyl-3-methyl-5-pyrazolyl-dimethylcarbamate, 2-dimethylamino-5,6-dimethyl-pyrimidin-4-yl-dimethylcarbamate, and the like.

The polyurethane used as the carrier may be prepared in a known manner by reacting polyisocyanates with higher-molecular compounds, containing at least two groups which are reactive with isocyanates, and optionally low-molecular chain lengthening agents and/or monofunctional chain stoppers.

Useful isocyanates include essentially any of the known aliphatic, cycloaliphatic, araliphatic, aromatic and heterocyclic polyisocyanates, such as are described, for example, by W. Siefken in Justus Liebigs Annalen der Chemie, 562, pages 75 to 136. Specific examples include ethylene-diisocyanate; tetramethylene-1,4-diisocyanate; hexamethylene-1,6-diisocyanate; dodecane-1,12-diisocyanate; cyclobutane-1,3-diisocyanate; cyclohexane- 1,3- and -1,4-diisocyanate as well as mixtures of these isomers; 1-isocyanato-3,3,5-trimethyl-4-isocyanatomethyl-cyclohexane as described in U.S. Pat. No. 3,401,190; hexahydrotoluylene-2,4- and -2,6-diisocyanate as well as mixtures of these isomers; hexahydrophenylene-1,3- and/or -1,4-diisocyanate; perhydrodiphenylmethane-2,4'- and/or -4,4'-diisocyanate; phenylene-1,3- and -1,4-diisocyanate; toluylene-2,4- and -2,6-diisocyanate as well as mixtures of these isomers; diphenylmethane-2,4'- and/or -4,4'-diisocyanate; naphthylene-1,5-diisocyanate; triphenylmethane-4,4',4"-triisocyanate; polyphenyl-polymethylene-polyisocyanates, such as are obtained by aniline/formaldehyde condensation and subsequent phosgenation of the product and as are described, for example, in British Pat. Nos. 874,430 and 848,671; m- and p-isocyanato-phenylsulphonylisocyanates as described in U.S. Pat. No. 3,454,606; perchlorinated arylpolyisocyanates, such as are described, for example, in U.S. Pat. No. 3,277,138; polyisocyanates containing carbodiimide groups, such as are described in U.S. Pat. No. 3,152,162; diisocyanates, such as are described in U.S. Pat. No. 3,492,330; polyisocyanates containing allophanate groups, such as are described, for example, in British Pat. No. 994,890, Belgian Pat. No. 761,626 and Dutch Published Patent Application No. 7,102,524; polyisocyanates containing isocyanurate groups, such as are described, for example, in U.S. Pat. No. 3,001,973, in German Pat. Nos. 1,022,789, 1,222,067 and 1,027,394 and in German Offenlegungsschriften Nos. 1,929,034 and 2,004,048; polyisocyanates containing urethane groups, such as are described, for example, in Belgian Pat. No. 752,261 or in U.S. Pat. No. 3,394,164; polyisocyanates containing acylated urea groups, as described in German Pat. No. 1,230,778; polyisocyanates containing biuret groups, such as are described, for example, in U.S. Pat Nos. 3,124,605 and 3,201,372 and in British Pat. No. 889,050; polyisocyanates which are prepared by telomerization reactions, such as are described, for example, in U.S. Pat. No. 3,654,106; polyisocyanates containing ester groups, such as are described, for example, in British Pat. Nos. 965,474 and 1,072,956, in U.S. Pat. No. 3,567,763 and in German Pat. No. 1,231,688; reaction products of the above-mentioned isocyanates with acetals, as described in German Pat. No. 1,072,385; and polyisocyanates containing polymeric fatty acid radicals as described in U.S. Pat. No. 3,455,883.

It is also possible to employ the distillation residues, containing isocyanate groups, obtained in the industrial preparation of isocyanates, optionally dissolved in one or more of the above-mentioned polyisocyanates. Furthermore, it is possible to use mixtures of any of the above-mentioned polyisocyanates. In general, however, the toluylene-diisocyanates and the diphenylmethane-diisocyanates are preferred polyisocyanates.

Further starting components for the preparation of the polyurethanes include compounds which have at least two hydrogen atoms which are reactive with isocyanates and which generally have molecular weights of from 400 to 10,000. While compounds containing amino groups, thiol groups or carboxyl groups may be used, it is generally preferred to use polyhydroxy compounds. Particularly preferred are compounds containing two to eight hydroxyl groups, especially those of molecular weight 800 to 10,000, preferably 1,000 to 6,000. Specific types of polyhydroxyl materials include polyesters, polyethers, polythioethers, polyacetals, polycarbonates and polyesteramides containing at least two, and in general 2 to 8, but preferably 2 to 4, hydroxyl groups, such as those which are generally known in the art for the preparation of homogeneous and cellular polyurethanes.

Examples of useful polyesters containing hydroxyl groups include reaction products of polyhydric, preferably dihydric and optionally also trihydric, alcohols with polybasic, preferably dibasic, carboxylic acids. Instead of the free polycarboxylic acids it is also possible to use the corresponding polycarboxylic acid anhydrides or corresponding polycarboxylic acid esters of lower alcohols or their mixtures for the preparation of the polyesters. The polycarboxylic acids can be of an aliphatic, cycloaliphatic, aromatic and/or heterocyclic nature and can be optionally substituted, for example by halogen atoms, and/or unsaturated. Examples of useful acids include succinic acid, adipic acid, suberic acid, azelaic acid, sebacic acid, phthalic acid, isophthalic acid, trimellitic acid, phthalic anhydride, tetrahydrophthalic anhydride, hexahydrophthalic anhydride, tetrachlorophthalic anhydride, endomethylenetetrahydrophthalic anhydride, glutaric anhydride, maleic acid, maleic anhydride, fumaric acid, dimeric and trimeric fatty acids, such as oleic acid, optionally mixed with monomeric fatty acids, terephthalic acid dimethyl ester, terephthalic acid bis-glycol ester, and the like. Examples of useful polyhydric alcohols include ethylene glycol, propylene 1,2-glycol and 1,3-glycol, butylene 1,4-glycol and 2,3-glycol, hexane-1,6-diol, octane-1,8-diol, neopentylglycol, cyclohexanedimethanol (1,4-bis-hydroxymethylcyclohexane), 2-methyl-propane-1,3-diol, glycerol, trimethylolpropane, hexane-1,2,6-triol, butane-1,2,4-triol, trimethylolethane, pentaerythritol, quinitol, mannitol, sorbitol, methyl glycoside, diethylene glycol, triethylene glycol, tetraethylene glycol, polyethylene glycols, dipropylene glycol, polypropylene glycols, dibutylene glycol, polybutylene glycols and the like. The polyesters may contain a proportion of terminal carboxyl groups. Polyesters of lactones, for example ε-caprolactone, or from hydroxycarboxylic acids, for example ω-hydroxy-caproic acid, can also be employed.

Suitable polyethers useful in preparing the polyurethanes are those containing at least two, and in general two to eight, preferably two to three, hydroxyl groups and which are also of the type generally known in the art. These may be prepared, for example, by the selfpolymerization of epoxides, such as ethylene oxide, propylene oxide, butylene oxide, tetrahydrofuran, styrene oxide or epichlorohydrin, for example in the presence of BF₃, or by addition of these epoxides, optionally mixed or successively, onto starting components containing reactive hydrogen atoms. Suitable starting components include water; ammonia; alcohols such as ethylene glycol, propylene 1,3-glycol or 1,2-glycol, trimethylol-propane, 4,4'-dihydroxy-diphenylpropane, and the like; and amines such as aniline, ethanolamine or ethylenediamine. Sucrose polyethers, such as are described, for example in German Auslegeschriften Nos. 1,176,358 and 1,064,938, can also be used. Those polyethers which contain predominant amounts (up to 90% by weight, relative to all the OH groups present in the polyether) of primary OH groups are preferred in many cases. Polyethers modified by vinyl polymers, such as are formed, for example, by polymerization of styrene and acrylonitrile in the presence of polyethers (U.S. Pat. Nos. 3,383,351, 3,304,273, 3,523,093 and 3,110,695 and German Pat. No. 1,152,536), are also suitable, as are polybutadienes containing OH groups.

Polythioethers which may be used include, in particular, the self-condensation products of thiodiglycol and/or the condensation products of thiodiglycol and other glycols, dicarboxylic acids, formaldehyde, aminocarboxylic acids or aminoalcohols. Depending on the co-components, the products are mixed polythioethers, polythioether-esters or polythioether-ester-amides.

Examples of useful polyacetals include the compounds which can be prepared from glycols, such as diethylene glycol, triethylene glycol, 4,4'-dihydroxyethoxydipenyldimethylmethane or hexanediol, and formaldehyde. Polyacetals which are suitable according to the invention can also be prepared by the polymerization of cyclic acetals.

Useful polycarbonates containing hydroxyl groups include those of the type which are generally know, such as can be prepared, for example, by reacting diols, such as propane-1,3-diol, butane-1,4-diol and/or hexane-1,6-diol, diethyleneglycol, triethylene glycol or tetraethylene glycol with diaryl carbonates, for example diphenyl carbonate, or phosgene.

The useful polyester-amides and polyamides include, for example, the predominantly linear condensation products obtained from polybasic saturated and unsaturated carboxylic acids or their anhydrides and polyhydric saturated and unsaturated aminoalcohols, diamines, polyamines and their mixtures.

Polyhydroxy compounds which already contain urethane groups or urea groups and optionally modified natural polyols, such as castor oil, carbohydrates or starch can also be used. It is also possible to employ addition products of alkylene oxides with phenol/formaldehyde resins or with urea/formaldehyde resins.

It is also possible, of course, to employ mixtures of the above-mentioned compounds which contain at least two hydrogen atoms which are reactive with isocyanates and which have molecular weights of from 400 to 10,000, for example mixtures of polyethers and polyesters.

Representatives of the many compounds which may be used according to the invention are known and are described, for example, in High Polymers, volume XVI, "Polyurethanes, Chemistry and Technology", edited by Saunders-Frisch, Interscience Publishers, New York, London, volume I, 1962, pages 32–42 and pages 44–54 and volume II, 1964, pages 5–6 and 198–199, and in Kunststoff-Handbuch (Plastics Handbook), volume VII, Vieweg-Hochtlen, Carl-Hanser-Verlag, Munich, 1966, pages 45–71.

Useful starting components which can be optionally employed also include compounds which contain at least two hydrogen atoms which are reactive towards isocyanates and which have molecular weights of from 32 to 400. Suitable compounds include compounds containing hydroxyl groups and/or amino groups and/or thiol groups and/or carboxyl groups. Presently preferred compounds are those containing hydroxyl groups and/or amino groups, which serve as chain lengthening agents or crosslinking agents. As a rule, these compounds contain 2 to 8 hydrogen atoms which are reactive with isocyanates, and preferably 2 or 3 reactive hydrogen atoms. Examples of suitable compounds include ethylene glycol, propylene 1,2-glycol and 1,3-glycol, butylene 1,4-glycol and 2,3-glycol, pentane-1,5-diol, hexane-1,6-diol, octane-1,8-diol, neopentylglycol, 1,4-bis-hydroxymethylcyclohexan e, 2-methyl-1,3-propanediol, glycerol, trimethylolpropane, hexane-1,2,6-triol, trimethylolethane, pentaerythritol, quinitol, mannitol, sorbitol, diethylene glycol, triethylene glycol, tetraethylene glycol, polyethylene glycols with a molecular weight of up to 400, dipropylene glycol, polypropylene glycols with a molecular weight of up to 400, dibutylene glycol, polybutylene glycols with a molecular weight of up to 400, 4,4'-dihydroxydiphenylpropane, dihydroxymethyl-hydroquinone, ethanolamine, diethanolamine, triethanolamine, 3-aminopropanol, ethylenediamine, 1,3-diaminopropane, 1-mercapto-3-aminopropane, 4-hydroxy- or -aminophthalic acid, succinic acid, adipic acid, hydrazine, N,N'-dimethyl-hydrazine, 4,4'-diaminodiphenylmethane, toluylenediamine, methylene-bis-chloroaniline, methylene-bis-anthranilic acid esters, diaminobenzoic acid esters and the isomeric chlorophenylenediamines. It is also possible to use mixtures of various compounds which contain at least two hydrogen atoms which are reactive towards isocyanates and which have molecular weights of from 32 to 400.

It is also possible to employ polyhydroxy compounds in which high-molecular polyadducts or polycondensates are contained in a finely dispersed or dissolved form. Modified polyhydroxy compounds of this type are obtained when polyaddition reactions (for example reactions between polyisocyanates and compounds containing amino functional groups) or polycondensation reactions (for example between formaldehyde and phenols and/or amines) are allowed to proceed directly in situ in the above-mentioned compounds containing hydroxyl groups. Processes of this type are known and are described, for example in German Auslegeschriften Nos. 1,168,075 and 1,260,142, and German Offenlegungsschriften Nos. 2,324,134, 2,423,984, 2,512,385, 2,513,815, 2,550,796, 2,550,797, 2,550,833 and 2,550,862. It is also possible as described in U.S. Pat. No. 3,869,413 or German Offenlegungsschrift No. 2,550,860, to prepare useful materials by mixing a ready-made aqueous polymer dispersion with a polyhydroxy compound and thereafter removing the water from the mixture.

When choosing the higher-molecular polyol component used for the preparation of the polyurethane, it must be taken into consideration that the finished polyurethane should not be swellable in water. The use of relatively large amounts of polyhydroxy compounds containing ethylene oxide units (polyethylene glycol polyethers or polyesters with diethylene glycol or triethylene glycol as the diol component is thus to be avoided. Preferably less than 30 percent by weight of polyols of this type are used. Most preferably less than 15 percent by weight of polyols and used. Hydrophobic polyesters, in particular those based on adipic acid and ethylene glycol and/or butanediol and/or neopentylglycol and/or hexanediol, polycarbonate-diols and polyetherpolyols based on propylene oxide or tetrahydrofuran are preferably employed. In some cases, it is also appropriate (especially if relatively large amounts of mineral fillers are incorporated into the polyurethane) to co-use castor oil as the polyol component in order to render the polyurethane hydrophobic.

Catalysts are frequently also used in the preparation of the polyurethanes. Catalysts which may be used are those of the type generally known in the art. Examples include tertiary amines, such as triethylamine, tributylamine, N-methyl-morpholine, N-ethyl-morpholine, N-cocomorpholine, N,N,N',N'-tetramethyl-ethylene-diamine, 1,4-diazabicyclo-(2,2,2)-octane, N-methyl-N'-dimethylaminoethyl-piperazine, N,N-dimethylbenzylamine, bis-(N,N-diethylaminoethyl) adipate, N,N-diethylbenzylamine, pentamethyldiethylenetriamine, N,N-dimethylcyclohexylamine, N,N,N',N'-tetramethyl-1,3-butanediamine, N,N-dimethyl-$\beta$-phenyletylamine, 1,2-dimethylimidazole and 2-methylimidazole. Mannich bases, which are also known in the art, obtained from secondary amines, such as dimethylamine, and aldehydes, preferably formaldehyde, or ketones, such as acetone, methyl ethyl ketone or cyclohexanone, and phenols, such as phenol, nonylphenol or bisphenol, can also be used as catalysts.

Examples of tertiary amines which contain hydrogen atoms which are active towards isocyanate groups and may be used as catalysts are triethanolamine, triisopropanolamine, N-methyldiethanolamine, N-ethyl-diethanolamine and N,N-dimethylethanolamine, and their reaction products with alkylene oxides, such as propylene oxide and/or ethylene oxide.

Further useful catalysts include sila-amines with carbon-silicon bonds, such as are described, for example, in U.S. Pat. No. 3,620,980, for example 2,2,4-trimethyl-2-silamorpholine and 1,3-diethylaminomethyl-tetramethyl-disiloxane.

Other useful catalysts include nitrogen-containing bases, such as tetraalkylammonium hydroxides; alkali metal hydroxides, such as sodium hydroxide; alkali metal phenolates, such as sodium phenolate; or alkali metal alcoholates, such as sodium methylate. Hexahydrotriazines can also be employed as catalysts.

Organic metal compounds, and in particular organic tin compounds, can also be used as catalysts. Preferred organic tin compounds include tin(II) salts of carboxylic acids, such as tin(II) acetate, tin(II) octoate, tin(II) ethylhexoate and tin(II) laurate, and tin(IV) compounds, such as for example, dibutyl-tin oxide, dibutyl-tin dichloride, dibutyl-tin diacetate, dibutyl-tin dilaurate, dibutyl-tin maleate or dioctyl-tin diacetate. The above-mentioned catalysts can, of course, also be employed as mixtures.

Yet further representatives of catalysts that can be used and details of the mode of action of the catalysts are known and are described in Kunststoff-Handbuch (Plastics Handbook), volume VII, edited by Vieweg and Hochtlen, Carl-Hanser-Verlag, Munich 1966, pages 96 to 102.

As a rule, the catalysts when employed, are employed in an amount between 0.001 and 10% by weight, relative to the amount of compounds which contain at least two hydrogen atoms which are reactive with isocyanates and which have a molecular weight of from 400 to 10,000.

The plasticizers, fillers, water-binding agents and dyestuffs customary in polyurethane chemistry can, of course, also be used in the preparation of the polyurethane. Examples of suitable plasticizers include phthalates, such as benzyl butyl phthalate and dioctyl phthalate, and esters of sebacic acid or adipic acid. Phthalates, in particular benzyl butyl phthalate, are preferred. Examples of fillers which may be used include carbon black, chalk, baryte, kaolin and aluminum silicates. Zeolites of the types known in the art are the presently preferred water-absorbing agents. Any of the known dyestuffs, for example organic or, preferably, inorganic colored pigments, and in particular iron oxide pigments, can be employed in order to impart the desired coloration to the collars according to the instant invention.

The polyurethanes which are used, according to the invention, as the carrier can be prepared in a manner which is in itself known, either by a single step process or by a prepolymer or semi-prepolymer process.

Thermoplastic polyurethanes such as are formed by reacting diisocyanates with higher-molecular dihydroxy compounds and low-molecular glycols, as chain lengthening agents, in a NCO/OH ratio between 0.97 and 1.05, are a class of carriers which are preferred according to the invention. Thermoplastic polyurethanes of this type are known and are described, for example, in British Pat. Nos. 1,210,737, 1,270,836, 1,075,274, 1,110,118, 1,025,970, 1,057,018, 1,087,743 and 849,136, German Pat. Nos. 1,189,268, 1,103,024, 1,106,958 and 1,106,959 and German Offenlegungsschriften Nos. 2,323,393 and 2,418,075.

The ectoparasiticidal active compound can be added to the thermoplastic polyurethanes, which are present, for example, in the form of granules, optionally together with plasticizers, fillers and dyestuffs, in suitable mixing devices, for example in drums or in an extruder. It is also possible to add the active compound directly during the preparation of the polyurethane, optionally mixed with one of the starting components, for example in a process of the type described in U.S. Pat. No. 3,963,679, in which polyisocyanates and polyhydroxy compounds are reacted with one another continuously in a twin-shaft screw machine. However, when using this process, care must be taken that the reaction temperature does not exceed the decomposition point of the carbamate used as the ectoparasiticide.

Another method of production consists in adding the ectoparasiticidal active compound to a cold-curing two-component polyurethane system comprising a prepolymer containing isocyanate groups, a polyhydroxy compound and a catalyst. These two component systems are known for the preparation of coatings, trowelling compositions and joint-filling compositions. In this case, it is appropriate to first mix the ectoparasiticide with the polyol component, which in general already contains the catalyst and, optionally, plasticizers, fillers and dyestuffs, then to stir this component with the isocyanate component.

It is also possible to add the ectoparasiticidal active compounds to solvent-free reactive systems which contain plasticizers and consist of a higher-molecular polyisocyanate component and a polyamine component, such as are described, for example, in German Offenlegungsschrift No. 2,488,133.

It is also possible, of course, to introduce the active compound into a solution of a polyurethane or polyurethane-urea and then to evaporate off the solvent. In this case also, relatively high temperatures must be avoided so that no decomposition of the carbamate occurs. Solutions of polyisocyanate polyaddition products in weakly polar, highly volatile solvents or solvent mixtures are therefore appropriately used. So-called "soft solvent" systems of this type described, for example, in U.S. Pat. No. 2,957,852, British Pat. No. 1,040,055, Belgian Pat. No. 643,811, U.S. Pat. Nos. 3,734,894, 3,609,112, 3,752,786, 3,936,409, 3,912,680, 3,867,350 and 3,857,809. Polar solvent systems (for example containing dimethylformamide or N-methyl-pyrrolidone) can also be used if the temperature in the drying step is kept sufficiently low.

It is possible to prepare animal collars based purely on polyurethane, for example by injection molding or reactive injection molding one of the thermoplastics mentioned, or allowing a reactive two-component system to react completely in a suitable mold. However, in many cases it is desirable to impregnate and/or coat a suitable carrier (for example a fabric made of natural (such as cotton) and/or synthetic fibers, leather, imitation leather or a porous or homogeneous plastic sheet) with one of the above-mentioned active compound containing thermoplastic polyurethanes, two-component reactive systems or single component polyurethanes, dissolved in solvents which can be easily evaporated. In general, this carrier is worn on the outside of the collar and the coating comprising the polyurethane containing the ectoparasiticide is on the inside. In this manner, it is possible to give the animal collar virtually any desired appearance.

The animal collars according to the invention are preferably used for livestock and/or pets, especially for cattle, dogs and cats. The collars according to the invention can be successfully employed against a number of harmful animal parasites (ectoparasites) from the class of *Arachnidae* and the class of insects.

Examples which may be mentioned of ectoparasites of the class of *Arachnidae*, which figure prominently in tropical, sub-tropical and temperate latitudes, are, from the family of *Ixodidae*, the Australian and South American one-host cattle tick (*Boophilus microplus*), the African one-host cattle tick (*Boophilus decoloratus*) and multi-host ticks which are parasitic on livestock and pets in all continents, such as *Rhipicephalus appendiculators, Rhipicephalus evertsi, Amblyomma variegatum, Amblyomma hebraeum, Amblyomma cayennense, Hyalomma truncatum, Dermacentor variabilis* and *Ixodes ricinus*, as well as, from the family of *Gamasidae*, the red poultry mite (*Dermanyssus gallinae*).

Examples of ectoparasites from the class of insects include *Mallophaga*, for example the dog biting louse (*Trichodectes canis*), the cattle biting louse (*Damalinea bovis*), the sheep biting louse (*Damalinea ovis*) and the poultry biting louse (*Eomenacanthus stramineus*); *Anoplura*, for example the cattle louse (*Haematopinus eurysternus*) and the pig louse (*Haematopinus suis*); *Diptera*, for example the sheep ked (*Melophagus ovinus*); and *Aphaniptera*, for example the dog flea (*Ctenocephalides canis*).

The active compound is not deposited on the surface of the polyurethane in the form of visible crystals, so that the collars according to the invention do not have a dusty appearance either on the upper side or on the underside. Nevertheless, the collars are active over a period of more than 4 months, as is illustrated in more detail in the Examples which follow. The release experiments show that the active compound is released continuously from the collars according to the invention over relatively long periods (even after prolonged storage of the collar). In contradistinction, most of the active compound has already diffused out of a comparable collar based on polyvinyl chloride after a short time, after which only a very small amount of the insecticide is still released per unit time.

The Examples which follow illustrate the present invention. Unless otherwise indicated, the amounts given are to be understood as parts by weight or % by weight.

I. SYSTEMS CONTAINING PLASTICIZER

EXAMPLE 1

| Component A: | Ethanediol/butanediol/adipic acid polyester (molecular weight 2,000/molar ratio ethanediol/butanediol: 7:3) | 30.0 parts |
|---|---|---|
| | Benzyl butyl phthalate | 22.2 parts |
| | Benzyldimethylamine | 0.2 part |
| | Zeolite paste (homogenous dispersion of 50 percent of sodium aluminum silicate in castor oil) | 7.5 parts |
| | Silicate filler (clay) | 37.0 parts |
| | In organic dyestuff (iron oxide pigment) | 3.1 parts |
| Component B: | Crude diphenylmethane-diisocyanate (31 percent NCO) (Industrial mixture, prepared by reaction of aniline with formaldehyde and subsequent phosgenation of the reaction product) | 5.0 parts |
| | Benzyl butyl phthalate | 5.0 parts |

81.8 kg of component A were homogeneously mixed with 10.0 kg of the active compound Propoxur. Thereafter, 8.2 kg of component B were mixed in homogeneously.

The reaction mixture had a processing time of about 2–3 hours. During this period, it was applied to a leather with a coating thickness of 2.2 to 2.5 mm by means of a doctor knife.

The mass reacted completely in the course of 12–14 hours to give a tack-free product which could then be cut into collars having an ectoparasiticidal action.

EXAMPLE 2

| Component A: | Butanediol/adipic acid polyester (molecular weight 2,000) | 30.0 parts |
|---|---|---|
| | Benzyl butyl phthalate | 22.2 parts |
| | Triethylenediamine | 0.2 part |
| | Zeolite paste (according to Ex. 1) | 7.5 parts |
| | Chalk | 37.0 parts |
| Component B: | Crude diphenylmethane-diisocyanate (according to Ex. 1) | 5.0 parts |
| | Benzyl butyl phthalate | 5.0 parts |

As a result of using triethylenediamine as the catalyst, the processing time was only about 30 minutes.

The preparation of the coating composition and the application onto the carrier was effected in a manner similar to that of Example 1. This formulation was particularly suitable for the continuous preparation of collars.

EXAMPLE 3

| Component A: | Polyester from Example 1 | 30.0 parts |
|---|---|---|
| | Benzyldimethylamine | 0.2 part |
| | Zeolite paste (according to Ex. 1) | 7.5 parts |
| | Benzyl butyl phthalate | 22.2 parts |
| | Filler (baryte) | 37.0 parts |
| Component B: | Industrial diphenylmethane-diisocyanate (according to Ex. 1) | 5.0 parts |
| | Benzyl butyl phthalate | 5.0 parts |

The coating of the carrier was carried out in a manner similar to Example 1.

II. PLASTICIZER-FREE SYSTEMS

EXAMPLE 4

| Component A: | Mixture consisting of 47% of a linear polypropylene glycol terminally modified with ethylene oxide (OH number 28), 47% of a polypropylene oxide obtained using trimethylolpropane as the starter and terminally modified with ethylene oxide, and 6% of diethylene glycol. | 55.0 parts |
|---|---|---|
| | Filler (chalk) | 22.1 parts |
| | Zeolite paste (according to Ex. 1) | 5.5 parts |
| | Nickel acetylacetonate | 0.6 part |
| | Dyestuff (iron oxide pigment) | 0.3 part |
| Component B: | Reaction product of 5 mols of diphenylmethane-4,4'-diisocyanate and 1 mol of tripropylene glycol | 16.5 parts |

This formulation was suitable for continuous coating. The mass reacted completely in about 15 minutes. The preparation of the coating composition and its application to the carrier was effected in a manner similar to Example 1.

EXAMPLE 5

| Component A: | Polyether/glycol mixture from Example 4 | 55.0 parts |
|---|---|---|
| | Filler (chalk) | 22.55 parts |
| | Zeolite paste (according to Ex. 1) | 5.5 parts |
| | triethylenediamine | 0.15 parts |
| | Dyestuff (iron oxide pigment, according to Ex. 1) | 0.3 part |
| Component B: | Reaction product of 5 mols of diphenylmethane-4,4'-diisocyanate and 1 mol of tripropylene glycol | 16.5 parts |

The formulation was particularly suitable for use in a discontinuous preparation in a manner similar to Example 1.

In Examples 6 to 17 which follow, the components listed in the Table which follows were in each case premixed in a drum mixer (the polyurethane elastomer was in the form of granules here) and then homogeneously mixed in an extruder in a known manner. A Reifenhauser S 45 extruder was employed for this purpose, the screw pressure being 50 kp/cm² and the screw speed being adjusted to 22 revolutions per minute and the temperature being adjusted to 130° C. in the intake zone and at the nozzle and to 160° C. in the middle of the screw.

TABLE

| EXAMPLE | 6 | 7 | 8 | 9 | 10 | 11 | 12 | 13 | 14 | 15 | 16 | 17 |
|---|---|---|---|---|---|---|---|---|---|---|---|---|
| Polyurethane I | 88 | 90 | 86 | 88 | 88 | — | — | — | — | — | — | — |
| Polyurethane II | — | — | — | — | — | 90 | 86 | 88 | — | — | — | — |
| Polyurethane III | — | — | — | — | — | — | — | — | 88 | 90 | 86 | 88 |
| Plasticizer | 2 | — | 2 | — | 2 | — | 2 | — | 2 | — | 2 | — |
| Propoxur | 10 | 10 | 10 | 10 | 10 | 10 | 10 | 10 | 10 | 10 | 10 | 10 |
| Dyestuff | — | — | 2 | 2 | — | — | 2 | 2 | — | — | 2 | 2 |

The three polyurethane thermoplastics used were prepared in a reaction screw as described in U.S. Pat. No. 3,963,679 from the following components:

POLYURETHANE I:

100 parts of a polyester of butanediol and adipic acid (molecular weight 2,000), 11 parts of 1,4-bis-($\beta$-hydroxyethoxy)-benzene and an amount of diphenylmethane-4,4'-diisocyanate corresponding to an NCO/OH ratio of 1.03.

POLYURETHANE II:

100 parts of a polyester of ethylene glycol, butanediol (molar ration 1:1) and adipic acid (molecular weight 2,000) 13 1 parts of butane-1,4-diol and an amount of diphenylmethane-4,4'-diisocyanate corresponding to an NCO/OH ratio of 1.03.

POLYURETHANE III:

50 parts of a polypropylene glycol ether (molecular weight 2,000), 50 parts of a polyester of butane-1,4-diol and adipic acid (molecular weight 2,000), 9 parts of butane-1,4-diol and an amount of diphenylmethane-4,4'-diisocyanate corresponding to an NCO/OH ratio of 1.03.

Benzyl butyl phthalate was used as the plasticizer and an iron oxide pigment was used as the dyestuff.

All the animal collars prepared according to Examples 6 to 17 exhibited no efflorescence of the Propoxur on the surface and uniformly released the active compound to the surroundings over several months.

EXAMPLE 18

20 g of Propoxur were dissolved in 50 g of methyl ethyl ketone at room temperature, while stirring occasionally. 25 g of N-methylpyrrolidone were then added and 25 g of a granular thermoplastic polyurethane were dissolved in the mixture thus obtained.

The solution was cast in the form of a film 1 mm thick and the solvents were removed in a drying cabinet at 100° to 150° C. in the course of 60 minutes. A homogeneous, transparent film was formed which contained 80 parts of Propoxur per 100 parts of polyurethane and from which the active compound did not effloresce, even upon prolonged storage.

The polyurethane was prepared by reacting 100 parts of a butanediol/ethylene glycol/adipic acid polyester (OH number: 51.7/molar ratio butanediol/ethylene glycol: 1:1), 7.5 parts of butane-1,4-diol and 31.3 parts of 4,4'-diisocyanatodiphenylmethane (NCO/OH=0.97) in a reaction screw, as described in example 1 a of U.S. Pat. No. 3,963,679 (incorporated herein by reference).

EVALUATION EXPERIMENT

The release of Propoxur from a collar, according to the invention, prepared by the method in Example 1 was compared with that from a conventional PVC collar containing Propoxur (as described in Example 5 of U.S. Pat. No. 3,852,416) in the following manner:

The release of Propoxur in water was followed in a rotary flask apparatus over 24 hours. The content of active compound in the release medium was determined calorimetrically, after hydrolysis to isopropoxyphenol.

2 g of the collar to be investigated (in one piece) and 200 ml of distilled water were put into each vessel of a Souder and Ellenbogen rotary flask apparatus. The release was effected at 37° C. and 25 revolutions/minute. Samples of 2 ml each were taken at the start and after 1, 6 and 24 hours.

2 ml of 2 N sodium hydroxide solution were added to each of the samples and the mixtures were left to stand for 30 minutes. After acidifying with 2.5 ml of 2 N hydrochoric acid, 4-nitrobenzenediazonium tetrafluoborate was added. The maximum extinction at 508 nm was measured.

In FIG. 1, the ordinate gives the release of active compound in per cent by weight, while the abscissa gives the number of hours (measuring time).

The individual curves in FIG. 1 relate to the following collars:

Curve A: Propoxur/PVC collar, shortly after preparation,
Curve B: Propoxur/PVC collar, stored at 20° C. for 8 months,
Curve C: Propoxur collar according to Example 1, shortly after preparation,
Curve D: Propoxur collar according to Example 1, stored at 20° C. for 8 months.

It can be seen that in contrast to the PVC collars, the collars according to the invention have a virtually linear release of active compound.

What is claimed is:

1. An animal collar having ectoparasiticidal activity, which comprises a plastic composition comprising from 75 to 98% by weight of a hydrophobic polyurethane which is not swellable in water and from 2 to 25% by weight of an ectoparasiticidal carbamate having a vapor pressure of from $10^{-4}$ to $10^{-6}$ mm Hg at 20° C.

2. An animal collar according to claim 1 wherein the polyurethane is a thermoplastic polyurethane.

3. An animal collar comprising a member selected from the group consisting of a textile material, leather, imitation leather or a flexible plastic material, said material being impregnated and/or coated with a plastic composition comprising from 75 to 98% by weight of a hydrophobic polyurethane which is not swellable in water and from 2 to 25% by weight of an ectoparasiticidal carbamate having a vapor pressure of from $10^{-4}$ to $10^{-6}$ mm Hg at 20° C.

4. An animal collar according to claim 3, wherein the polyurethane is a cold-curing two-component system.

5. A method of protecting or freeing an animal from ectoparasites which comprises fitting the animal with a collar having ectoparasiticidal activity, which comprises a plastic composition comprising from 75 to 98% by weight of a hydrophobic polyurethane which is not swellable in water and from 2 to 25% by weight of an ectoparasiticidal carbamate having a vapor pressure of from $10^{-4}$ to $10^{-6}$ mm Hg at 20° C.

6. A method of protecting or freeing an animal from ectoparasites which comprises fitting the animal with a collar comprising a member selected from the group consisting of a textile material, leather, imitation leather or a flexible plastic material, said material being impregnated and/or coated with a plastic composition comprising from 75 to 98% by weight of a hydrophobic polyurethane which is not swellable in water and from 2 to 25% by weight of an ectoparasiticidal carbamate having a vapor pressure of from $10^{-4}$ to $10^{-6}$ mm Hg.

7. The animal collar of claim 1 wherein said plastic composition comprises from 85 to 95% by weight of said polyurethane and from 5 to 15% by weight of said carbamate.

8. The animal collar of claim 1 wherein the polyurethane absorbs less than 2% by weight of water by swelling when it is stored in water at 20° C. for 24 hours.

9. The animal collar of claim 1 wherein the polyurethane absorbs less than 0.5% by weight of water by swelling when it is stored in water at 20° C. for 24 hours.

10. The animal collar of claim 1 wherein the carbamate is 2-isopropoxyphenyl N-methyl-carbamate.

11. The animal collar of claim 1 wherein the polyurethane is a cold-curing two-component system.

* * * * *